United States Patent [19]

Iwamori et al.

[11] Patent Number: 5,260,198
[45] Date of Patent: Nov. 9, 1993

[54] CLONED TYROSINE PHENOL-LYASE GENE, RECOMBINANT PLASMID CONTAINING THE SAME AND ESCHERICHIA COLI TRANSFORMED WITH THE SAME

[75] Inventors: Satoru Iwamori; Toshihiro Oikawa; Setsuo Yoshino, all of Mobara; Kenichi Ishiwata, Yokohama, all of Japan

[73] Assignee: Mitsui Toatsu Chemicals, Inc., Tokyo, Japan

[21] Appl. No.: 677,413

[22] Filed: Mar. 29, 1991

[30] Foreign Application Priority Data

Mar. 31, 1990 [JP] Japan .................................. 2-82992

[51] Int. Cl.$^5$ ...................... C12N 15/00; C12N 15/67; C12N 15/70; C12N 15/60
[52] U.S. Cl. ............................ 435/252.33; 435/252.3; 435/252.33; 435/370.1; 435/69.1; 536/23.2; 735/74; 735/79; 735/44; 735/73
[58] Field of Search ................. 435/69.1, 252.3, 320.1, 435/232; 536/27

[56] References Cited

U.S. PATENT DOCUMENTS

| 5,112,749 | 5/1992 | Brey, III et al. ................. 435/122.3 |
| 5,114,853 | 5/1992 | Makiao et al. ..................... 435/190 |

FOREIGN PATENT DOCUMENTS

| 0394479 | 6/1989 | European Pat. Off. ........... 435/69.1 |
| 62-259589 | 11/1987 | Japan .................................. 435/69.1 |
| 63-157982 | 6/1988 | Japan .................................. 435/69.1 |
| 63-226682 | 9/1988 | Japan .................................. 435/69.1 |

OTHER PUBLICATIONS

Patent Abstracts of Japan, vol. 12, No. 143 (C-492)(2990), Apr. 30, 1988.
Abstracts of the 89th Annual Meeting of the American Society for Microbiology, 14–18 May 1989.
Syusev, V. A., et al., 1980, Biokhimiya, 45(5):889–895; (pp. 683–688 in translation by Plenum Publishing Corp.).
Kumagai, H., et al., 1972, Agricultural and Biological Chemistry, 36(3): 472–482.
Demidkira, T. V., et al., 1984, Biokhimiya, 49(1): 32–37; (pp. 27–31 in translation by Plenum Publishing Corp.).
Tano, K., et al., 1988, Gene 64(2): 305–312.
Yanisch-Perron, C., et al., 1985, Gene 33: 103–119.
Makoff, A. J., et al., 1988, Biochemical Society Transactions 16: 48–49.
Makaroff, C. A., et al., 1983, The Journal of Biological Chemistry 258(17): 10586–10593.
Foor, F., et al., 1989, Abstracts of The Annual Meeting of the American Society for Microbiology, 1989, p. 188.
Pharmacia, Inc. Molecular Biologicals Catalogue, 1984, p. 63.
de Boer, H. A., et al., 1983, Horizons in Biochemistry and Biophysics, 7: 205–248.

*Primary Examiner*—Robert A. Wax
*Assistant Examiner*—William W. Moore
*Attorney, Agent, or Firm*—Burns, Doane, Swecker & Mathis

[57] ABSTRACT

Disclosed is a cloned tyrosine phenol-lyase gene which encodes an amino acid sequence represented by the formula [I], which can be expressed in the absence of tyrosine in culturing medium. A recombinant vector containing the tyrosine phenol-lyase gene as well as *E. coli* transformants capable of producing tyrosine phenol-lyase are also disclosed.

10 Claims, 7 Drawing Sheets

Fig. 2a

BssH II
```
GCGCGCATAG TGACGCGCTA TTTTCACGCA TGATAAATCC CGCATGATGG TGTCGTATTA        60

TTTCCACCTC AATTCTGAGG TTATTGTTAT ATCTTCCTGT GCATTTCATC TATGCACCAG       120

ACTTATTCGA CGCGCATTTT TCTGCGTATG AAAATGGATA ACTGGAGAAA TAAAC ATG        178
                                                              Met
                                                                1
```

```
AAC TAT CCT GCC GAG CCT TTC CGC ATT AAA AGT GTT GAA ACC GTA TCA        226
Asn Tyr Pro Ala Glu Pro Phe Arg Ile Lys Ser Val Glu Thr Val Ser
         5                  10                  15

ATG ATC TCA CGC GAT GAG CGT GTT AAA AAA ATG CAA GAA GCG GGC TAT        274
Met Ile Ser Arg Asp Glu Arg Val Lys Lys Met Gln Glu Ala Gly Tyr
         20                  25                  30

AAC ACG TTT TTA CTG AAT TCA AAG GAT ATC TAC ATC GAT CTG CTG ACA        322
Asn Thr Phe Leu Leu Asn Ser Lys Asp Ile Tyr Ile Asp Leu Leu Thr
     35                  40                  45

GAC AGC GGT ACA AAT GCC ATG AGT GAC AAG CAG TGG GCA GGG ATG ATG        370
Asp Ser Gly Thr Asn Ala Met Ser Asp Lys Gln Trp Ala Gly Met Met
 50                  55                  60                  65

ATT GGT GAT GAA GCC TAC GCA GGC AGT GAA AAC TTC TAC CAT CTC GAA        418
Ile Gly Asp Glu Ala Tyr Ala Gly Ser Glu Asn Phe Tyr His Leu Glu
                 70                  75                  80

AAA ACG GTG AAA GAG TTG TTT GGT TTC AAA CAC ATC GTT CCA ACC CAC        466
Lys Thr Val Lys Glu Leu Phe Gly Phe Lys His Ile Val Pro Thr His
             85                  90                  95

CAG GGA CGC GGG GCG GAA AAC CTG CTC TCG CAG CTG GCC ATT AAG CCC        514
Gln Gly Arg Gly Ala Glu Asn Leu Leu Ser Gln Leu Ala Ile Lys Pro
         100                 105                 110
```

Fig. 2b

```
GGT CAA TAT GTC GCA GGA AAT ATG TAC TTT ACA ACA ACC CGC TTC CAT           562
Gly Gln Tyr Val Ala Gly Asn Met Tyr Phe Thr Thr Thr Arg Phe His
    115             120             125

CAG GAA AAA AAT GGC GCA ACC TTT GTG GAT ATT GTC CGC GAT GAA GCA           610
Gln Glu Lys Asn Gly Ala Thr Phe Val Asp Ile Val Arg Asp Glu Ala
130             135             140             145

CAT GAC GCC AGC CTG AAT CTC CCC TTT AAA GGT AAT ATT GAC CTG AAT           658
His Asp Ala Ser Leu Asn Leu Pro Phe Lys Gly Asn Ile Asp Leu Asn
                150             155             160

AAA TTA GCG ACG CTC ATT AAA GAA AAA GGC GCC GAG AAC ATC GCC TAT           706
Lys Leu Ala Thr Leu Ile Lys Glu Lys Gly Ala Glu Asn Ile Ala Tyr
            165             170             175

ATC TGC CTT GCG GTC ACC GTG AAT CTG GCG GGT GGG CAG CCT GTT TCA           754
Ile Cys Leu Ala Val Thr Val Asn Leu Ala Gly Gly Gln Pro Val Ser
        180             185             190

ATG GCG AAT ATG CGT GCC GTA CAT GAA ATG GCC AGC ACG TAT GGC ATT           802
Met Ala Asn Met Arg Ala Val His Glu Met Ala Ser Thr Tyr Gly Ile
    195             200             205

AAG ATC TAT TAC GAT GCT ACC CGT TGC GTT GAA AAT GCC TAT TTT ATC           850
Lys Ile Tyr Tyr Asp Ala Thr Arg Cys Val Glu Asn Ala Tyr Phe Ile
210             215             220             225

AAA GAG CAG GAG GCG GGC TAC GAG AAC GTC AGT ATC AAA GAT ATC GTG           898
Lys Glu Gln Glu Ala Gly Tyr Glu Asn Val Ser Ile Lys Asp Ile Val
                230             235             240

CAT GAA ATG TTC AGC TAT GCC GAT GGG TGC ACC ATG AGC GGT AAA AAA           946
His Glu Met Phe Ser Tyr Ala Asp Gly Cys Thr Met Ser Gly Lys Lys
            245             250             255
```

Fig. 2c

| | |
|---|---:|
| GAT TGT CTG GTG AAT ATC GGC GGC TTG TTG TGT ATG AAC GAT GAG GAG<br>Asp Cys Leu Val Asn Ile Gly Gly Phe Leu Cys Met Asn Asp Glu Glu<br>            260                     265                  270 | 994 |
| ATG TTC TCA GCG GCA AAA GAG TTG GTT GTC GTT TAT GAA GGT ATG CCG<br>Met Phe Ser Ala Ala Lys Glu Leu Val Val Val Tyr Glu Gly Met Pro<br>            275                     280                  285 | 1042 |
| TCA TAC GGC GGG CTG GCC GGT CGG GAT ATG GAA GCA ATG GCT ATT GGG<br>Ser Tyr Gly Gly Leu Ala Gly Arg Asp Met Glu Ala Met Ala Ile Gly<br>290                   295                     300                 305 | 1090 |
| CTA CGT GAA GCC ATG CAG TAT GAA TAT ATT GAA CAT CGG GTC AAA CAG<br>Leu Arg Glu Ala Met Gln Tyr Glu Tyr Ile Glu His Arg Val Lys Gln<br>            310                     315                  320 | 1138 |
| GTG CGC TAT CTG GGC GAT AAA CTC CGT GAA GCC GGC GTA CCC ATT GTT<br>Val Arg Tyr Leu Gly Asp Lys Leu Arg Glu Ala Gly Val Pro Ile Val<br>            325                     330                  335 | 1186 |
| GAA CCG ACG GGC GGA CAT GCG GTA TTT CTT GAT GCT CGT CGT TTC TGT<br>Glu Pro Thr Gly Gly His Ala Val Phe Leu Asp Ala Arg Arg Phe Cys<br>            340                     345                  350 | 1234 |
| CCA CAC CTG ACG CAG GAT CAG TTC CCT GCG CAG AGC CTG GCA GCC AGC<br>Pro His Leu Thr Gln Asp Gln Phe Pro Ala Gln Ser Leu Ala Ala Ser<br>            355                     360                  365 | 1282 |

Fig. 2d

```
ATC TAT ATG GAA ACC GGC GTG CGA AGT ATG GAA CGT GGA ATT GTT TCC         1330
Ile Tyr Met Glu Thr Gly Val Arg Ser Met Glu Arg Gly Ile Val Ser
370             375             380             385

GCC GGT CGT AGC AAG GAA ACG GGG GAG AAC CAT AGC CCC AAA CTG GAG         1378
Ala Gly Arg Ser Lys Glu Thr Gly Glu Asn His Ser Pro Lys Leu Glu
                390             395             400

ACG GTA CGT CTC ACT ATT CCA CGC CGT GTT TAC ACT TAC GCG CAC ATG         1426
Thr Val Arg Leu Thr Ile Pro Arg Arg Val Tyr Thr Tyr Ala His Met
            405             410             415

GAT GTT ATT GCC GAT GGC ATC ATT AAA CTG TAC CAG CAT AAA GAA GAT         1474
Asp Val Ile Ala Asp Gly Ile Ile Lys Leu Tyr Gln His Lys Glu Asp
        420             425             430

ATT CGT GGT CTG ACG TTT GTT TAC GAA CCT AAA CAA CTT CGC TTC TTT         1522
Ile Arg Gly Leu Thr Phe Val Tyr Glu Pro Lys Gln Leu Arg Phe Phe
    435             440             445

Hae III
ACT GCG CGT TTT GAC TTT ATT TAATACAACC CTGGCCCCGC AGGGGGCC              1571
Thr Ala Arg Phe Asp Phe Ile ***
450             455
```

CLONED TYROSINE PHENOL-LYASE GENE, RECOMBINANT PLASMID CONTAINING THE SAME AND ESCHERICHIA COLI TRANSFORMED WITH THE SAME

BACKGROUND OF THE INVENTION

I. Field of the Invention

This invention relates to a cloned tyrosine phenol-lyase gene, recombinant plasmids containing the tyrosine phenol-lyase gene, and to *E. coli* transformed with the recombinant plasmid, which are useful for the production of tyrosine phenol-lyase.

II. Description of the Related Art

Tyrosine phenol-lyase is a so called multifunctional enzyme, which catalyzes various reactions such as synthesis reactions of L-tyrosine and L-DOPA (Yamada, H. and Kumagai, H. (1975) Adv. Appl. Microbiol., vol. 19, pp. 249-288) and which is industrially important.

Various bacteria are known to produce tyrosine phenol-lyase. Among these, those belonging to genera Escherichia, Citrobacter, Aerobacter, Proteus and Erwinia which genera belong to Family Enterobacteriaceae have high tyrosine phenol-lyase activities (Yamada et al, supra).

Further, DNA fragments containing tyrosine phenol-lyase gene originating from *Erwinia herbicola* ATCC-21434 or *Escherichia freundii* AJ-2608 have been isolated and *E. coli* transformants containing these genes have tyrosine phenol-lyase activity (Japanese Laid Open Patent Application (Kokai) Nos. 259589/87 and 222682/88, respectively).

However, the tyrosine phenol-lyase activities of these microorganisms are low so that the microorganisms cannot be employed industrially. Further, when culturing these microorganisms, it is necessary to add to the culture medium tyrosine (Yamada et al, supra, or Japanese Laid Open Patent Application (Kokai) No. 259589/87) or isopropyl-β-thiogalactoside (Japanese Laid Open Patent Application (Kokai) No. 222682/88). Further, if tyrosine is added to the culture medium in, for example, the production of DOPA, the product is likely to be contaminated with tyrosine On the other hand, isopropyl-β-thiogalactoside is extremely expensive, so that it cannot be used in an industrial scale.

SUMMARY OF THE INVENTION

Accordingly, an object of the present invention is to provide a means for producing tyrosine phenol-lyase in an industrial scale with high efficiency without using an induction substance such as tyrosine or isopropyl-β-thiogalactoside.

The present inventors intensively studied the method of producing tyrosine phenol-lyase with high efficiency. As a result, the present inventors succeeded in isolating a DNA fragment containing tyrosine phenol-lyase gene originating from *Erwinia herbicola*, determining the nucleotide sequence of the gene, preparing a novel recombinant plasmid in which the tyrosine phenol-lyase structural gene is inserted at the downstream region of a promoter, which recombinant plasmid can express the tyrosine phenol-lyase gene in the absence of tyrosine in the culture medium and in preparation an *E. coli* transformant transformed with the recombinant plasmid, and the present inventors found that this *E. coli* transformant can produce a prominently large amount of tyrosine phenol-lyase without adding an induction substance, thereby completing the present invention.

That is, the present invention provides a cloned tyrosine phenol-lyase gene which encodes an amino acid sequence represented by the following formula [I] [SEQ ID:3], which can be expressed in the absence of tyrosine in a culturing medium.

[I]

Met Asn Tyr Pro Ala Glu Pro Phe Arg Ile Lys Ser Val Glu

Thr Val Ser Met Ile Ser Arg Asp Glu Arg Val Lys Lys Met

Gln Glu Ala Gly Tyr Asn Thr Phe Leu Leu Asn Ser Lys Asp

Ile Tyr Ile Asp Leu Leu Thr Asp Ser Gly Thr Asn Ala Met

Ser Asp Lys Gln Trp Ala Gly Met Met Ile Gly Asp Glu Ala

Tyr Ala Gly Ser Glu Asn Phe Tyr His Leu Glu Lys Thr Val

Lys Glu Leu Phe Gly Phe Lys His Ile Val Pro Thr His Gln

Gly Arg Gly Ala Glu Asn Leu Leu Ser Gln Leu Ala Ile Lys

Pro Gly Gln Tyr Val Ala Gly Asn Met Tyr Phe Thr Thr Thr

Arg Phe His Gln Glu Lys Asn Gly Ala Thr Phe Val Asp Ile

Val Arg Asp Glu Ala His Asp Ala Ser Leu Asn Leu Pro Phe

Lys Gly Asn Ile Asp Leu Asn Lys Leu Ala Thr Leu Ile Lys

Glu Lys Gly Ala Glu Asn Ile Ala Tyr Ile Cys Leu Ala Val

Thr Val Asn Leu Ala Gly Gly Gln Pro Val Ser Met Ala Asn

Met Arg Ala Val His Glu Met Ala Ser Thr Tyr Gly Ile Lys

Ile Tyr Tyr Asp Ala Thr Arg Cys Val Glu Asn Ala Tyr Phe

Ile Lys Glu Gln Glu Ala Gly Tyr Glu Asn Val Ser Ile Lys

Asp Ile Val His Glu Met Phe Ser Tyr Ala Asp Gly Cys Thr

Met Ser Gly Lys Lys Asp Cys Leu Val Asn Ile Gly Gly Phe

Leu Cys Met Asn Asp Glu Glu Met Phe Ser Ala Ala Lys Glu

Leu Val Val Val Tyr Glu Gly Met Pro Ser Tyr Gly Gly Leu

Ala Gly Arg Asp Met Glu Ala Met Ala Ile Gly Leu Arg Glu

Ala Met Gln Tyr Glu Tyr Ile Glu His Arg Val Lys Gln Val

Arg Tyr Leu Gly Asp Lys Leu Arg Glu Ala Gly Val Pro Ile

Val Glu Pro Thr Gly Gly His Ala Val Phe Leu Asp Ala Arg

Arg Phe Cys Pro His Leu Thr Gln Asp Gln Phe Pro Ala Gln

Ser Leu Ala Ala Ser Ile Tyr Met Glu Thr Gly Val Arg Ser

Met Glu Arg Gly Ile Val Ser Ala Gly Arg Ser Lys Glu Thr

Gly Glu Asn His Ser Pro Lys Leu Glu Thr Val Arg Leu Thr

Ile Pro Arg Arg Val Tyr Thr Tyr Ala His Met Asp Val Ile

Ala Asp Gly Ile Ile Lys Leu Tyr Gln His Lys Glu Asp Ile

Arg Gly Leu Thr Phe Val Tyr Glu Pro Lys Gln Leu Arg Phe

Phe Thr Ala Arg Phe Asp Phe Ile

The present invention also provides a recombinant plasmid comprising the cloned tyrosine phenol-lyase gene of the present invention at a downstream region of a promoter, which is capable of producing tyrosine phenol-lyase in a host cell in the absence of tyrosine in the culture medium.

The present invention further provides *E. coli* transformed with the recombinant plasmid of the present invention, which is capable of producing tyrosine phenol-lyase in the absence of tyrosine in the culture medium.

By the present invention, it was first attained to produce tyrosine phenol-lyase with high efficiency without adding an induction substance such as tyrosine to the culture medium. By the present invention, tyrosine phenol-lyase can be produced in an industrial scale.

BRIEF DESCRIPTION OF THE DRAWINGS

FIGS. 2a, 2b, 2c and 2d shows the nucleotide sequence [SEQ ID NO:2] of tyrosine phenol-lyase gene together with the amino acid sequence [SEQ ID NO:3] encoded thereby;

DETAILED DESCRIPTION OF THE PREFERRED EMBODIMENTS

Figure 1:
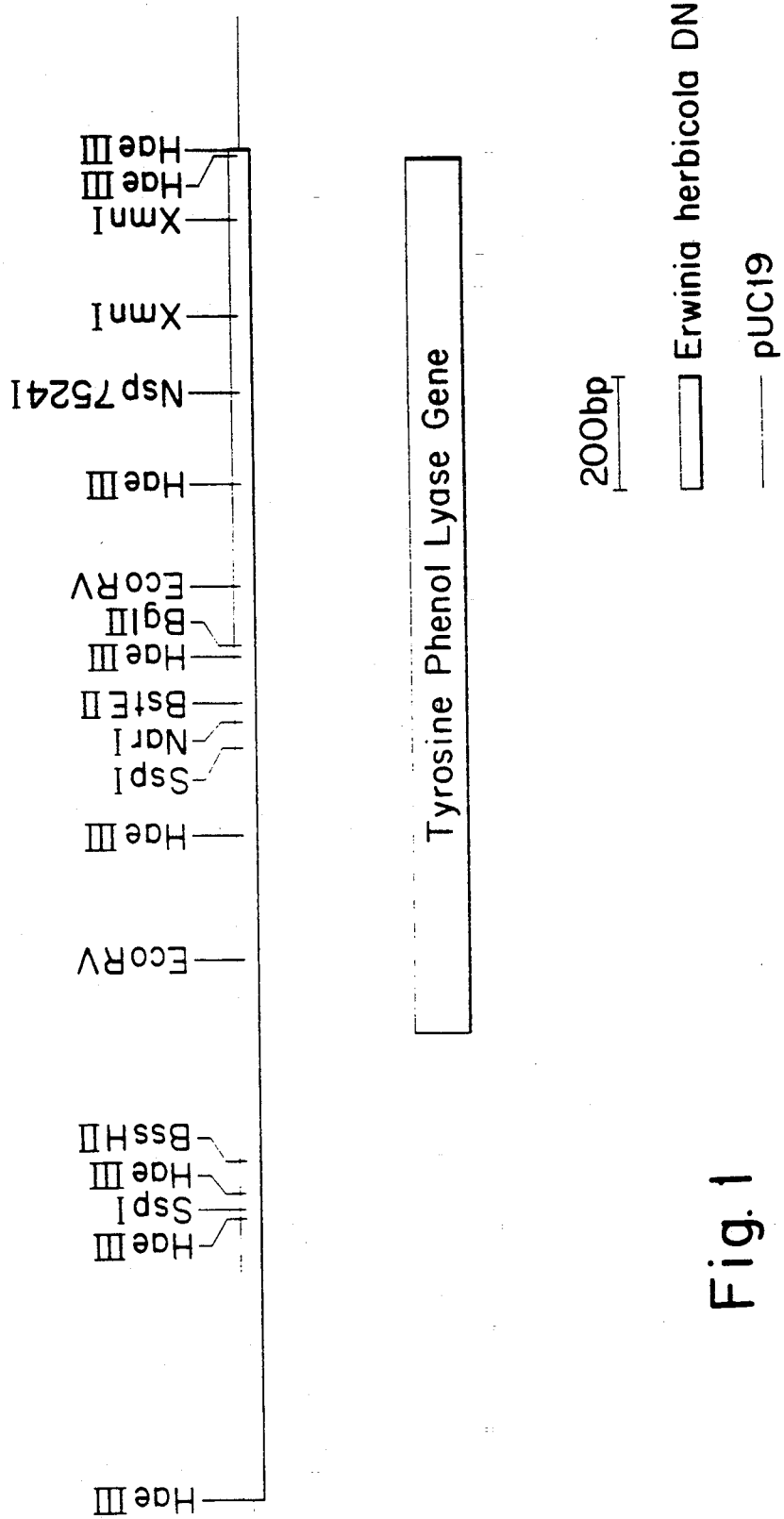
FIG. 1 shows a restriction map of a DNA insert originating from *Erwinia herbicola* in a recombinant plasmid pEH2, as well as the approximate position of the tyrosine phenol-lyase gene therein.

As described above, the cloned tyrosine phenol-lyase gene of the present invention encodes the amino acid sequence represented by the above-described formula [I]. An example of the cloned gene of the present invention has a nucleotide sequence represented by the following formula [II] [SEQ ID NO:1].

ATG AAC TAT CCT GCC GAG CCT TTC CGC ATT AAA AGT GTT GAA    [II]
ACC GTA TCA ATG ATC TCA CGC GAT GAG CGT GTT AAA AAA ATG
CAA GAA GCG GGC TAT AAC ACG TTT TTA CTG AAT TCA AAG GAT
ATC TAC ATC GAT CTG CTG ACA GAC AGC GGT ACA AAT GCC ATG
AGT GAC AAG CAG TGG GCA GGG ATG ATG ATT GGT GAT GAA GCC
TAC GCA GGC AGT GAA AAC TTC TAC CAT CTC GAA AAA ACG GTG
AAA GAG TTG TTT GGT TTC AAA CAC ATC GTT CCA ACC CAC CAG
GGA CGC GGG GCG GAA AAC CTG CTC TCG CAG CTG GCC ATT AAG
CCC GGT CAA TAT GTC GCA GGA AAT ATG TAC TTT ACA ACA ACC
CGC TTC CAT CAG GAA AAA AAT GGC GCA ACC TTT GTG GAT ATT
GTC CGC GAT GAA GCA CAT GAC GCC AGC CTG AAT CTC CCC TTT
AAA GGT AAT ATT GAC CTG AAT AAA TTA GCG ACG CTC ATT AAA
GAA AAA GGC GCC GAG AAC ATC GCC TAT ATC TGC CTT GCG GTC
ACC GTG AAT CTG GCG GGT GGG CAG CCT GTT TCA ATG GCG AAT
ATG CGT GCC GTA CAT GAA ATG GCC AGC ACG TAT GGC ATT AAG
ATC TAT TAC GAT GCT ACC CGT TGC GTT GAA AAT GCC TAT TTT
ATC AAA GAG CAG GAG GCG GGC TAC GAG AAC GTC AGT ATC AAA
GAT ATC GTG CAT GAA ATG TTC AGC TAT GCC GAT GGG TGC ACC
ATG AGC GGT AAA AAA GAT TGT CTG GTG AAT ATC GGC GGC TTC
TTG TGT ATG AAC GAT GAG GAG ATG TTC TCA GCG GCA AAA GAG
TTG GTT GTC GTT TAT GAA GGT ATG CCG TCA TAC GGC GGG CTG
GCC GGT CGG GAT ATG GAA GCA ATG GCT ATT GGG CTA CGT GAA
GCC ATG CAG TAT GAA TAT ATT GAA CAT CGG GTC AAA CAG GTG
CGC TAT CTG GGC GAT AAA CTC CGT GAA GCC GGC GTA CCC ATT
GTT GAA CCG ACG GGC GGA CAT GCG GTA TTT CTT GAT GCT CGT
CGT TTC TGT CCA CAC CTG ACG CAG GAT CAG TTC CCT GCG CAG
AGC CTG GCA GCC AGC ATC TAT ATG GAA ACC GGC GTG CGA AGT
ATG GAA CGT GGA ATT GTT TCC GCC GGT CGT AGC AAG GAA ACG
GGG GAG AAC CAT AGC CCC AAA CTG GAG ACG GTA CGT CTC ACT
ATT CCA CGC CGT GTT TAC ACT TAC GCG CAC ATG GAT GTT ATT

-continued

```
GCC GAT GGC ATC ATT AAA CTG TAC CAG CAT AAA GAA GAT ATT

CGT GGT CTG ACG TTT GTT TAC GAA CCT AAA CAA CTT CGC TTC

TTT ACT GCG CGT TTT GAC TTT ATT
```

The gene of the present invention may be originated from a microorganism having tyrosine phenol-lyase activity, such as those belonging to the genera Escherichia, Citrobacter, Aerobacter, Proteus and Erwinia. A preferred specific example of a microorganism producing tyrosine phenol-lyase is *Erwinia herbicola* MT-10509 (FERM P-11385).

The cloned tyrosine phenol-lyase gene of the present invention may be obtained, for example, by the following method:

A microorganism having tyrosine phenol-lyase activity is cultured and the chromosomal DNAs are extracted and purified from the microorganism by, for example, the phenol method (Saito, H. et al (1963) Biochem. Biophys. Acta, vol. 72, pp. 619–629).

The chromosomal DNAs are then digested with an appropriate restriction enzyme and the resulting DNA fragments are ligated with a plasmid vector which can replicate in an *E. coli* cell using a DNA ligase. Various restriction enzymes may be employed if the degree of digestion is controlled by controlling the amount of the restriction enzyme used and/or the reaction time Preferred examples of the restriction enzymes may include Hpa II, Acc I, Sau3A I, Hae III and Sma I. As the plasmid vector, those which can replicate in *E. coli* may be employed. Preferred examples of the plasmid include ColE1 plasmids such as pBR322, pUC19, pKK223-3 and the like which are commercially available. The ligation of the DNA fragments and the plasmid vector may be carried out by digesting the plasmid vector with the same restriction enzyme as used in the digestion of the chromosomal DNAs or with a restriction enzyme which yields the same cohesive end as formed by the restriction enzyme used for the digestion of the chromosomal DNAs, and ligating the digested plasmid vector with the DNA fragments by the aid of a ligase. As the DNA ligase, those originating from T4 phages may preferably be employed. Only the chromosomal DNA fragments with a specific size separated by a conventional method such as sucrose density gradient centrifugation or agarose gel electrophoresis may be ligated with the plasmid vector.

*E. coli* with no tyrosine phenol-lyase-producing ability is then transformed with the resulting recombinant DNAs. Preferred examples of the *E. coli* with no tyrosine phenol-lyase-producing ability include *E. coli* MC-1061 and *E. coli* JM-83 which are known in the art.

The transformants which acquired the tyrosine phenol-lyase-producing ability are then selected. The selection of the transformants which acquired the tyrosine phenol-lyase ability may be carried out, for example, by forming colonies of the transformants on an agar plate of L-medium to which tyrosine is added, spraying 4-aminoantipyrine onto the agar plate and by selecting the transformant forming a colony whose periphery is turned red by the spraying.

From the recombinant plasmid contained in these transformants, DNA fragments carrying the tyrosine phenol-lyase gene may be separated. This step may be accomplished by, for example, the alkaline extraction method (Brinboim, H. et al. (1979) Nucleic Acids Res., vol. 7, pp. 1513–1523).

The resulting recombinant plasmid may be again introduced into *E. coli* if desired by, for example, the calcium chloride method (Mandel, O. et al. (1970), J. Mol. Biol., vol. 53, pp. 159–162).

The present invention also provides a recombinant vector comprising the cloned tyrosine phenol-lyase gene of the present invention as mentioned above. The recombinant vector of the present invention can produce tyrosine phenol-lyase in the absence of tyrosine in the culture medium. The recombinant plasmid vector may be obtained by inserting the chromosomal DNA fragment containing the tyrosine phenol-lyase gene into a plasmid vector having a strong promoter This can be accomplished by, for example, cutting out a DNA fragment containing the tyrosine phenol-lyase gene from the plasmid pEH2 and inserting the fragment in a plasmid vector at a downstream region of a strong promoter of the vector. Preferred examples of the promoter with high activity include trp promoter, lacUV5 promoter, tac promoter and λ PL promoter. Examples of the recombinant plasmids of the present invention which can produce tyrosine phenol-lyase with high efficiency in *E. coli* cells without adding tyrosine to the culture medium include plasmid pEH21 and pCE26 which are described in detail in the actual working examples described below. Needless to say, the recombinant vector of the present invention contains, as the conventional expression vectors, a replication origin which enables the vector to replicate in the host cell and an SD sequence necessary for the translation in addition to the chromosomal DNA fragment containing the tyrosine phenol-lyase gene and the promoter. The recombinant vector preferably contains a selection marker such as a region giving drug resistance or temperature sensitivity, as well as a terminator. Vectors containing the replication origin, promoter, SD sequence, selection marker and the terminator are well-known in the art and many of them are commercially available. In the present invention, such commercially available vectors may be employed.

The present invention further provides *E. coli* transformed with the recombinant vector of the present invention, which can produce tyrosine phenol-lyase in the absence of tyrosine in the culture medium. The transformation may be carried out by, for example, the calcium chloride method mentioned above. *E. coli* containing the above-mentioned plasmid pEH21 designated as *Escherichia coli* MT-10516 (or MC-1061/pEH21) and *E. coli* containing the above-mentioned plasmid pCE26 designated as *Escherichia coli* MT-10519 (or MC-1061/pCE26) have been deposited with Fermentation Research Institute of Japan under the Budapest Treaty under accession numbers of FERM BP-3259 and FERM BP-3287, respectively.

By culturing *E. coli* in the present invention, tyrosine phenol-lyase may be obtained in the culture medium The culturing of the *E. coli* of the present invention may be carried out by the conventional method. That is, the

*E. coli* of the present invention may be cultured aerobically in the presence of a carbon source, nitrogen source and inorganic ions, and if required, amino acids and vitamins.

The culture medium thus obtained may be used as it is as an enzyme source of tyrosine phenol-lyase. Crude enzyme extract, purified enzyme live *E. coli* cells and treated *E. coli* cells obtained from the culture medium may also be used as an enzyme source of tyrosine phenol-lyase. The tyrosine phenol-lyase may be purified from the culture medium by a conventional method well-known in the art.

The invention will now be described by way of examples thereof It should be noted that the examples are presented for illustration purpose only and should not be interpreted in any restrictive way.

EXAMPLE 1

(a) Separation of Chromosomal DNAs of *Erwinia herbicola*

*Erwinia herbicola* MT-10509 (FERM P-11385) was inoculated to 1 liter of L medium (10 g/l of bactotryptone, 5 g/l of yeast extract and 5 g/l of sodium chloride, pH 7.2) and cultured under shaking at 30° C. for 15 hours. The cells were then collected by centrifugation.

The collected cells were suspended in 160 ml of 0.15M NaCl-50 mM EDTA (pH 8.0) solution and 160 mg of lysozyme was added thereto. The mixture was gently stirred at 37° C. for 20 minutes and then 4 ml of 20% SDS solution was added thereto. The resulting mixture was then left to stand for 20 minutes at 65° C.. Then 8 mg of Proteinase K (commercially available from Boehringer Mannheim) was added and the mixture was left to stand at 37° C. for 1 hour.

To the resulting mixture, 160 ml of phenol saturated with 0.15M NaCl-50 mM EDTA solution (pH 8.0) was added. After gentle stirring, the mixture was centrifuged (10,000 rpm, 15 minutes), and the supernatant was recovered.

To the supernatant thus obtained, twice volume of cold ethanol was added and fibrous precipitation was collected by winding the same around a glass rod. The collected fibrous precipitation was sequentially immersed in ethanol solutions with concentrations of 70%, 80% and 90% in that order for several minutes in each ethanol solution. The thus treated fibrous precipitate was dried and then dissolved in 40 ml of 0.1M NaCl-0.15M sodium citrate solution (pH 7.0).

To the crude DNA solution thus obtained, 200 µl of 6 mg/ml ribonuclease A (commercially available from Boehringer Mannheim) was added and the resulting mixture was left to stand at 37° C. for 1.5 hours.

To this solution, was added 40 ml of phenol saturated with 0.15M NaCl-50 mM EDTA (pH 8.0), and the solution was gently stirred. The resultant was then centrifuged (10,000 rpm, 15 minutes) and the supernatant was recovered.

To the supernatant thus obtained, two volumes of cold ethanol was added and the fibrous precipitate was collected by winding the same around a glass rod. The collected fibrous precipitate was sequentially immersed in ethanol solutions with concentrations of 70%, 80% and 90% in that order for several minutes in each ethanol solution. The thus treated fibrous precipitate was dried and then dissolved in 20 ml of 10 mM Tris-HCl (pH 8.0)-1 mM EDTA solution (hereinafter referred to as "TE buffer").

The DNA solution thus obtained was dialyzed against 2 liters of TE buffer to obtain 10 ml of TE buffer containing 2 mg of chromosomal DNAs.

(b) Preparation of Chromosomal DNA Fragments

To 450 µl (containing 90 µg of DNAs) aliquot of the TE buffer containing the chromosomal DNAs prepared in (a), 10 units of restriction enzyme Hae III (commercially available from Boehringer Mannheim) was added and the resulting mixture was mixed with 500 µl of reaction medium containing 10 mM Tris-HCl (pH 7.5), 7 mM $MgCl_2$, 60 mM of NaCl and 7 mM of 2-mercaptoethanol. The reaction mixture was left to stand at 37° C. for 1 hour to partially cut the chromosomal DNAs.

To the resulting solution, equivolume of phenol/chloroform (phenol:chloroform=1:1 (v/v)) mixture saturated with TE buffer was added and the resultant was gently stirred. The mixture was then centrifuged (15,000 rpm, 5 minutes) and the supernatant was recovered.

To the supernatant thus obtained, two volumes of cold ethanol was added and the generated precipitate was dissolved in 100 µl of TE buffer after drying. The thus obtained DNA solution was subjected to sucrose density gradient centrifugation (20° C., 26,000 rpm, 24 hours) with a gradient of 10–40% by weight of sucrose, and two fractions of about 2–5 kbp and 5–10 kbp were collected. After dialyzing each of the collected fractions against TE buffer, DNAs were collected by the ethanol precipitation method and the collected DNAs were dissolved in TE buffer.

(c) Ligation of Chromosomal DNA Fragments and Plasmid Vector

Ten micrograms of pUC 19 (commercially available from Takara Shuzo) was completely digested with restriction enzyme Sma I (commercially available from Nippon Gene) and the obtained digest was treated with alkaline phosphatase. Each of the chromosomal DNA fragments prepared in (b) was mixed with 0.25 µg each of the plasmid and the mixture was allowed to react in 0.4 ml of a reaction medium containing 5 mM $MgCl_2$, 10 mM dithiothreitol, 1 mM ATP and 66 mM Tris-HCl buffer (pH 7.5) in the presence of 5 units of T4 DNA ligase (commercially available from Boehringer Mannheim) at 16° C. for 16 hours.

The mixture after the reaction was used as it was for the transformation of *E. coli*.

(d) Cloning of Tyrosine Phenol-lyase Gene

With the reaction mixture containing the recombinant plasmid prepared in (c), the *E. coli* was transformed. *E. coli* MC-1061 having no ability to produce tyrosine phenol-lyase was inoculated with 5 ml of L medium (10 g/l of bactotryptone, 5 g/l of yeast extract and 5 g/l of sodium chloride, pH 7.2) and was cultured under shaking at 37° C. for 3 hours. The cells were then collected by centrifugation.

The cells were suspended in 2 ml of 0.1M $CaCl_2$ solution and the suspension was left to stand at 0° C. for 30 minutes. The cells were then collected by centrifugation and were suspended in 4 ml of $CaCl_2$ solution.

The cell suspension thus prepared was equally divided into two test tubes (2 ml each). To each of the test tubes, the reaction mixture prepared in (c) was added and the resultant was left to stand at 0° C. for 3 hours, followed by incubation at 42° C. for 2 minutes.

The cells were collected by centrifugation and 5 ml each of L medium was added to the cells. Each of the cell suspensions was cultured at 37° C. for 30 minutes and the cells were collected by centrifugation.

After suspending the cells in 10 ml each of 0.85% NaCl, the cells collected by centrifugation were suspended in 1 ml each of 0.85% NaCl.

The cell suspensions thus prepared were applied on L medium containing 100 mg/l of ampicillin, 20 g/l of L-tyrosine and 15 g/l of agar and the cells were incubated at 37° C. for 1 day.

To the agar plates on which colonies were formed, aqueous solutions of (i) 1.4 wt % sodium hydrogen carbonate, (ii) 0.85 wt % 4-aminoantipyrine and (iii) 5.4 wt % potassium ferricyanide were sequentially sprayed in the order mentioned and those strains constituting the colonies of which the peripheries turned in red were selected.

From the agar plates on which the E. coli transformed with the recombinant plasmid prepared by using the fractions of 2–5 kbp chromosomal DNAs, three tyrosine phenol-lyase-producing strains were obtained. Among these, the E. coli strain separated from the representative colony was named Escherichia coli MT-10515.

(e) Separation of Recombinant Plasmid Contained in E. coli

From Escherichia coli MT-10515, the recombinant plasmid was separated by the method as follows:

E. coli MT-10515 was inoculated to 100 ml of L medium and was cultured under shaking at 37° C. for 15 hours, followed by collection of the cells by centrifugation.

The collected cells were suspended in 4 ml of 50 mM glucose-25 mM Tris-HCl-10 mM EDTA (pH 8.0) solution containing 4 mg of lysozyme.

To the suspension, 8 ml of 0.2N NaOH-1 wt % SDS solution was added and the resulting mixture was stirred. To the resultant, 6 ml of 3M sodium acetate solution (pH 5.2) was added and the resulting mixture was left to stand at 4° C. for 5 minutes. The mixture was then centrifuged and the supernatant was recovered.

To the thus obtained an equivolume of phenol/chloroform mixture (phenol:chloroform=1:1) saturated with TE buffer was added and the resulting mixture was gently stirred. The resultant was centrifuged (10,000 rpm, 5 minutes) and the supernatant was recovered.

To the thus obtained supernatant, two volumes of cold ethanol was added. The generated precipitate was dried and dissolved in TE buffer.

To the thus prepared DNA solution, 20 µl of 1 mg/ml ribonuclease A (commercially available from Boehringer Mannheim) was added and the resultant was left to stand at 37° C. for 20 minutes.

To the resulting mixture, an equivolume of phenol/chloroform mixture (phenol:chloroform=1:1) was added and the resultant was gently stirred. The resulting mixture was then centrifuged and the supernatant was recovered.

The thus prepared DNA solution was purified by column chromatography on Bio-Gel A-50m (commercially available from Bio-Rad), and the plasmid DNA was recovered by the ethanol precipitation method.

By the process described above, about 1.2 mg of plasmid DNA was obtained, which was then dissolved in 1 ml of TE buffer.

In the analysis of the recombinant plasmid hereinbelow described, the plasmid obtained as mentioned above was used.

(f) Analysis of Recombinant Plasmid

The plasmid separated from E. coli MT-10515 was named pEH2. This recombinant plasmid has a size of about 4.8 kbp, and a DNA insert with a size of about 2.1 kbp was observed by digesting the plasmid with restriction enzymes Sac I and Pst I.

The restriction map of the DNA insert in the plasmid pEH2 is shown in FIG. 1.

(g) Confirmation of Reproducibility of Transformation

With the recombinant plasmid pEH2 separated in (e), E. coli MC-1061 having no tyrosine phenol-lyase-producing ability was transformed by the same manner as in (d), and the transformants were applied on L medium agar plates containing 100 mg/l of ampicillin and 20 g/l of L-tyrosine. The formed colonies were checked for their tyrosine phenol-lyase-producing ability by the 4-aminoantipyrine method as in (d). As a result, the peripheries of all colonies turned red. Thus, it was confirmed that a DNA fragment containing tyrosine phenol-lyase gene exists in pEH2.

(h) Subcloning and Analysis of DNA Fragment

Various DNA fragments lacking a part of the DNA insert in pEH2 were prepared and were separately inserted into the polylinker region downstream of the tac promoter in an expression vector pKK223-3 (commercially available from Pharmacia) by using a ligase. With the recombinant plasmids thus prepared, E. coli MC-1061 was transformed in the same manner as in (d), and the transformants were applied on L medium agar plates containing 100 mg/l of ampicillin and 20 g/l of L-tyrosine. The formed colonies were examined for their tyrosine phenol-lyase-producing ability by the 4-aminoantipyrine method as in (d) to determine the approximate position of the tyrosine phenol-lyase gene, which is shown in FIG. 1. The nucleotide sequence of the BssH II-Hae III DNA insert with a size of 1.6 kbp which was assumed to contain the tyrosine phenol-lyase gene was determined by the dideoxy method (Sanger, F. et al (1977), Proc. Natl. Acad. Sci. USA, vol. 74, pp. 5463–5467) using a vector of M13mp series (Messing, J. (1983), Methods in Enzymology, vol. 101, pp. 20–78). As a result, in the nucleotide sequence determined, the existence of an open reading frame shown in FIG. 2 was confirmed.

(i) Construction of Plasmid Highly Expressing Tyrosine Phenol-lyase Gene

One microgram of plasmid pKK223-3 (commercially available from Pharmacia) was completely digested with restriction enzymes Sma I and Pst I (both are commercially available from Nippon Gene) and the digest was treated with alkaline phosphatase, followed by collection of DNAs by the ethanol precipitation method to collect vector DNAs.

On the other hand, plasmid pEH2 was extracted in the same manner as in (e). Two microgram aliquots of the plasmid were completely digested with restriction enzyme BssH II (commercially available from Nippon Gene), and the digest was sequentially subjected to phenol treatment and ethanol precipitation. The resultant was treated with 5 units of Klenow Fragment (commercially available from Takara Shuzo) at 37° C.

for 1 hour to blunt the ends of the DNA fragments. The resultant was subjected to phenol treatment and ethanol precipitation, and was then completely digested with restriction enzyme Pst I (commercially available from Nippon Gene). The DNAs in the resulting reaction mixture were then subjected to 0.8% agarose gel electrophoresis and the portion of the gel which contained the DNA with a size of about 1.6 kb was cut out. The DNA was collected by electroelution and ethanol precipitation so as to prepare a DNA insert containing the tyrosine phenol-lyase gene.

Figure 3:
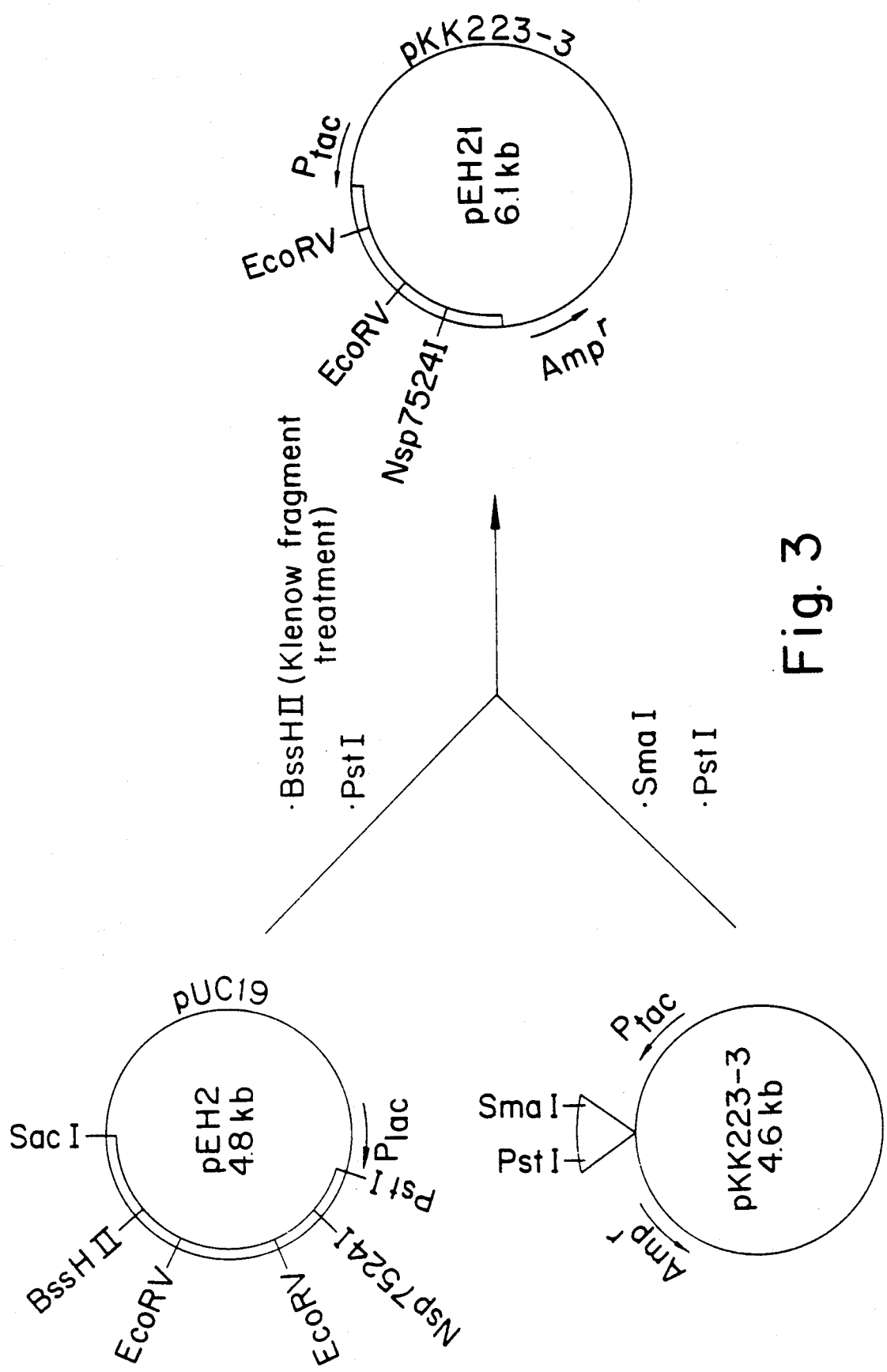
FIG. 3 shows a restriction map of a recombinant plasmid pEH21 according to the present invention as well as a construction process thereof.

The vector DNA dissolved in TE buffer and the DNA insert containing the tyrosine phenol-lyase gene were mixed and were allowed to react in 0.1 ml of a reaction mixture containing 5 mM MgCl$_2$, 10 mM dithiothreitol, 1 mM ATP and 66 mM Tris-HCl buffer (pH 7.5) in the presence of 300 units of T4 DNA ligase (commercially available from Boehringer Mannheim) at 16° C. for 4 hours. With the as obtained reaction mixture, *E. coli* MC-1061 lacking the tyrosine phenol-lyase-producing ability was transformed in the same manner as in (d) and the transformants were applied on L medium agar plates containing 100 mg/l of ampicillin and 20 g/l of L-tyrosine. The formed colonies were examined for their tyrosine phenol-lyase-producing ability by the 4-aminoantipyrine method as in (d), and tyrosine phenol-lyase-producing ability was observed in about 1000 strains. Four strains were selected from the thus obtained transformants and the plasmids were extracted therefrom as in (e). All of the thus obtained plasmid had a size of about 6.2 kb and had the same restriction map. The thus obtained plasmid was named pEH21. The restriction map of pEH21 is shown in FIG. 3. The *E. coli* transformed with pEH21 was named *Escherichia coli* MT-10516 and was deposited with Fermentation Research Institute of Japan under the Budapest Treaty under an accession number of FERM BP-3259.

EXAMPLE 2

One microgram of plasmid pUC118 (commercially available from Takara Shuzo) was completely digested with restriction enzymes Sma I and Pst I (both are commercially available from Nippon Gene), and the digest was treated with alkaline phosphatase, followed by the collection of the vector DNAs by ethanol precipitation.

On the other hand, the plasmid pEH2 was extracted as in (e) and the DNA insert of about 1.6 kb containing the tyrosine phenol-lyase gene was prepared as mentioned above. The DNA insert containing the tyrosine phenol-lyase gene was ligated with the vector DNA under the same conditions as in Example 1 and *E. coli* JM101 was transformed with the resulting recombinant plasmid in the same manner as in (d). From the colonies formed on L medium agar plates containing 100 mg/l of ampicillin, a plasmid was extracted and this plasmid was named pCE22.

A single stranded DNA was prepared from *E. coli* JM101 containing the plasmid pCE 22 by using a helper phage M13 K07 according to the following method: *E. coli* JM101 containing pCE22 was precultured in 2YT medium (1.6 wt % of bactotryptone, 1.0 wt % of yeast extract, 0.5 wt % of sodium chloride) containing 150 μg/ml of ampicillin. To 5 ml of fresh 2YT medium containing 150 μg/ml of ampicillin, the precultured medium was added in an amount to attain an absorbance at 600 nm of 0.02-0.05. The resultant was incubated at 37° C. until the absorbance at 600 nm reached 0.1-0.2.

Then 30 μl of a helper phage solution of M13 K07 (commercially available from Takara Shuzo) was added to the culture medium and the resulting medium was gently shaken at 37° C. for 30 minutes. Kanamycin was then added to the medium to a concentration of 70 μg/ml and the resulting medium was incubated under shaking at 37° C. for 14 hours. The culture medium was then transferred to a micro centrifugal tube and was centrifuged (8000 g, 5 minutes), followed by recovery of the supernatant. Per 1 ml of the supernatant, 200 μl of PEG-NaCl solution (20 wt % of polyethylene glycol, 2.5M NaCl) was added and the mixture was stirred well, followed by standing at room temperature for 15 minutes. The resulting mixture was centrifuged (8000 g, 5 minutes) and the supernatant was completely removed. The precipitate was dissolved in 100 μl of TE buffer. To the thus obtained solution, 50 μl of phenol saturated with TE buffer was added and the resultant was shaken for about 10 seconds, followed by being left to stand for about 10 minutes. To the resultant, 50 μl of a mixture of chloroform/isoamyl alcohol (24:1 (v/v)) was added and the resultant was centrifuged for 5 minutes after being left to stand for about 10 seconds. The supernatant (aqueous layer) was transferred to another micro centrifugal tube. To the supernatant thus obtained, 10 μl of sodium acetate was added and then 250 μl of iced ethanol was added. DNAs were collected by ethanol precipitation and the obtained precipitate was dissolved in 50 μl of TE buffer to obtain 10 μg of single stranded DNA of pCE22.

By using a synthetic primer with a nucleotide sequence [SEQ ID NO:6] of 5'-GGATAGTTCATATG-TATTTCTCCAG-3', the bases (AAC) at the immediate upstream the initiation codon ATG of the tyrosine phenol-lyase gene in the thus obtained single-stranded DNA was converted to CAT according to the method of site-directed mutagenesis so as to create Nde I restriction site. The method of site-directed mutagenesis employed was in accordance with the method of Fritz Eckstein et al (Taylor J. W. et al. (1985) Nucl. Acids Res., Vol. 13, pp. 8749-8785; Nakamaye K. et al., (1986) Nucl Acids Res., Vol. 13, pp. 9679-9698; Sayers, J. R. et al. (1988) Nucl. Acids Res., Vol. 13, pp. 791-802).

Figure 4:
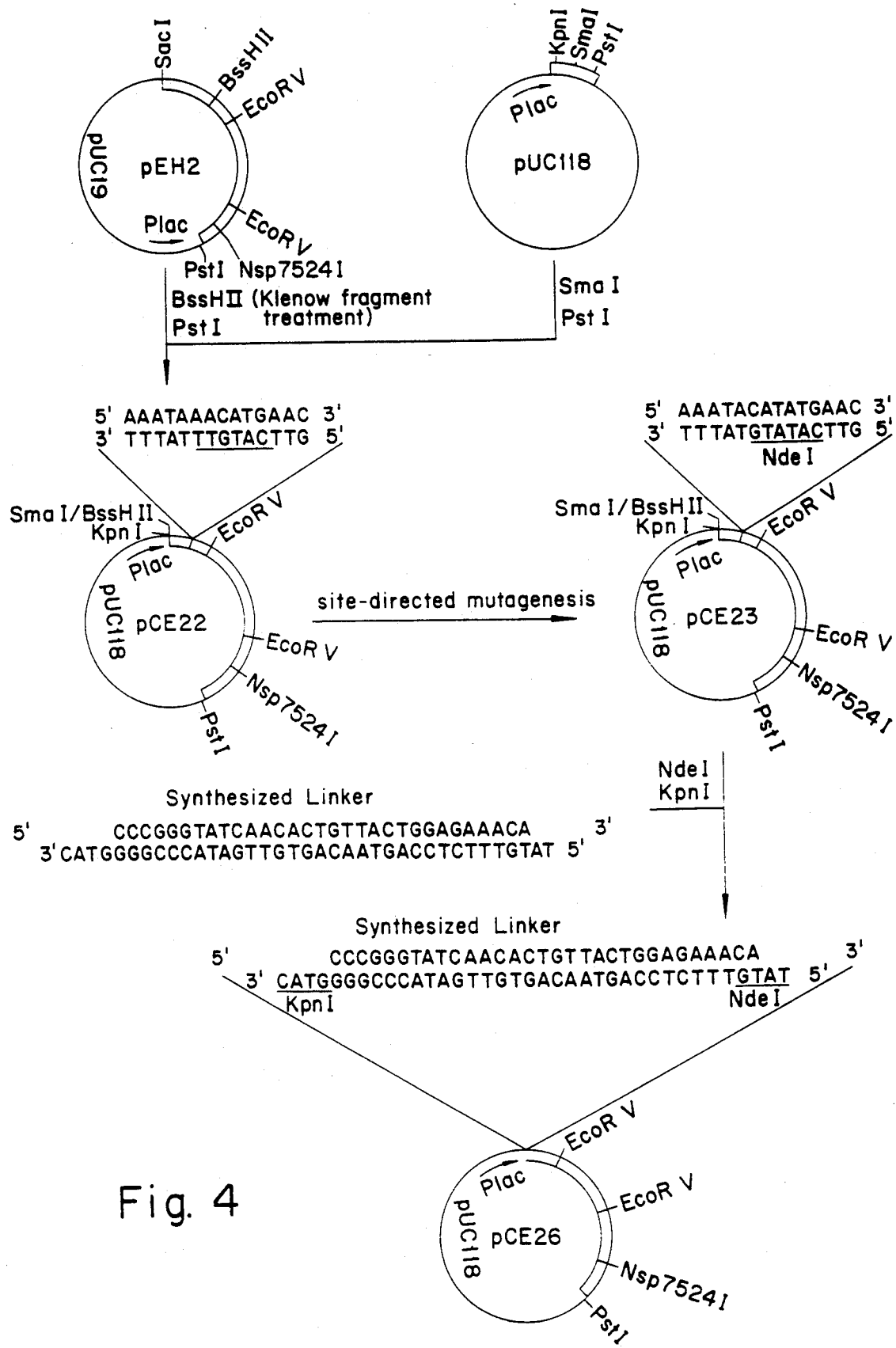
FIG. 4 shows a restriction map of a recombinant plasmid pCE26 according to the present invention as well as a construction process thereof.

Synthetic linkers having nucleotide sequences [SEQ ID NO:4] and [SEQ ID NO:5] of 5'-CCCGGGTAT-CAACACTGTTACTGGAGAAACA-3' and 5'-TATGTTTCTCCAGTAACAGTGTT-GATACCCGGGGTAC-3' in the amount of about 0.01 μg each were treated with T4 polynucleotide kinase (commercially available from Nippon Gene) in 0.1 ml of a reaction medium containing 10 mM MgCl$_2$, 7 mM dithiothreitol, 1 mM ATP and 100 mM Tris-HCl buffer (pH 8.0) at 37° C. for 30 minutes. The resultant was then heated at 70° C. for 10 minutes. On the other hand, 1 μg of pCE23 was completely digested with restriction enzymes Nde I (commercially available from Nippon Gene) and Kpn I (commercially available from Toyobo) and the DNAs were collected by ethanol precipitation after phenol treatment The thus prepared DNAs were mixed with 5 μl each of the synthetic linkers and the mixture was allowed to react in 0.1 ml of a reaction mixture containing 5 mM MgCl$_2$, 10 mM dithiothreitol, 1 mM ATP and 66 mM Tris-HCl buffer (pH 7.5) in the presence of 300 units of T4 DNA ligase (commercially available from Boehringer Mannheim) at 4° C. for 16 hours. With the thus obtained reaction mixture as it was, *E. coli* MC-1061 lacking the tyrosine phenol-lyase-producing ability was transformed in the same manner as in (d) and the transformants were applied on L medium agar plates containing 100 mg/l of ampicillin and 20 g/l of L-tyrosine. The formed colonies were examined for their tyrosine phenol-lyase-producing ability by the 4-aminoantipyrine method as in (d). As a result, about 100 strains produced tyrosine phenol-lyase. Four strains were selected from the thus prepared transformants and plasmids were extracted therefrom according to the method described in (e). All of the plasmids thus obtained had a size of about 4.6 kb and contained a DNA insert of about 1.4 kb, and had the same restriction map. The thus obtained plasmid was named pCE26. The restriction map of pCE26 is shown in FIG. 4. E. coli MC-1061 transformed with pCE26 was named Escherichia coli MT-10519 and was deposited with Fermentation Research Institute of Japan under the Budapest Treaty under an accession number of FERM BP-3287.

(j) Production of Tyrosine Phenol-lyase

E. coli MT-10516 and MT-10519 were respectively inoculated to 100 ml of L medium containing 0 or 20 g/l of L-tyrosine and cultured at 37° C. for 20 hours under shaking. The cells were then collected by centrifugation.

The tyrosine phenol-lyase activity of these cells were measured as follows: After washing the cells, the cells were suspended in 10 ml of 10 mM pyrophosphate buffer (pH 8.5) containing 0.1 mM pyridoxal phosphate. Cell extracts containing no cells were prepared by ultrasonication and the resulting solution was added to 90 ml of a reaction medium containing 70 g/l of L-serine, 17 g/l of phenol and 17 g/l of ammonium acetate whose pH was adjusted to 8.5 by aqueous ammonia and the reaction was allowed to occur at 37° C. for 1 hour under gentle stirring. The amount of the formed L-tyrosine was determined by high performance liquid chromatography according to the method by Kondo et al (Kondo, N. et al (1984) Agric. Biol. Chem. vol. 48, pp. 1595–1601).

The tyrosine phenol-lyase activities of the tested strains are shown in Table 1. It should be noted that one unit of the tyrosine phenol-lyase activity is the amount of the enzyme which can produce 1 μmol of tyrosine per 1 minute at 37° C..

As can be seen from Table 1, with MT-10516 and MT-10519 strains, high enzyme activities were observed even when no tyrosine was added to the medium.

TABLE 1

| Strain | Concentration of Tyrosine Added in Culturing (g/l) | Enzyme Activity (U/g wet cells) |
| --- | --- | --- |
| MT-10516 | 0 | 25.9 |
|  | 20 | 26.1 |
| MT-10519 | 0 | 81.6 |
|  | 20 | 89.9 |

COMPARATIVE EXAMPLE 1

For comparison, E. coli MC-1061 used as a host, Erwinia herbicola MT-10509 used as a source of chromosomal DNAs and E. coli-10515 containing the plasmid pEH2 were cultured in the same manner as in Example 3 and the tyrosine phenol-lyase activities were determined. The results are shown in Table 2.

TABLE 2

| Strain | Concentration of Tyrosine Added in Culturing (g/l) | Enzyme Activity (U/g wet cells) |
| --- | --- | --- |
| MC-1061 | 0 | 0 |
|  | 20 | 0 |
| MT-10509 | 0 | 1.5 |
|  | 20 | 11.6 |
| MT-10515 | 0 | 6.4 |
|  | 20 | 11.0 |

As can be seen from Table 2, as for MT-10509 strain, substantially no enzyme activity was observed when no tyrosine was added to the culture medium and the enzyme activity was observed only when tyrosine was added to the medium. As for MT-10515 strain, although enzyme activity was observed even in the absence of tyrosine, the enzyme activity was about half of that observed when tyrosine was added.

COMPARATIVE EXAMPLE 2

From Erwinia herbicola ATCC 21434, chromosomal DNAs were extracted and a Sau3A I - Pst I DNA fragment with a size of 1.7 kb containing an Eco RI site encodes a polypeptide that encodes a phenotype of β-tyrosinase activity was inserted in the Bam HI-Pst I site of a plasmid vector pUC18 in accordance with the method described in Japanese Laid Open Patent Application No. 259589/87. The thus prepared plasmid was named pSP17. An Sma I-Hind III DNA fragment of 1.7 kb which has β-tyrosinase activity was separated from pSP17 and the Hind III end thereof was made blunt with Klenow fragment. The DNA fragment was then inserted into the Sma I site of plasmid vector pKK223-3 to prepare two plasmid vectors pSP18 and pSP19 in which the orientation of the DNA fragment with respect to the tac promoter is opposite each other. E. coli MC-1061 was transformed with each of the plasmids pSP18 and pSP19 and the tyrosine phenol-lyase activities of the obtained transformants were determined as in Example 3. The results are shown in Table 3.

TABLE 3

| Strain | Concentration of Tyrosine Added in Culturing (g/l) | Enzyme Activity (U/g wet cells) |
| --- | --- | --- |
| MC-1061/ pSP18 | 0 | 4.5 |
|  | 20 | 8.9 |
| MC-1061/ pSP19 | 0 | 0.5 |
|  | 20 | 2.8 |

As can be seen from Table 3, the tyrosine phenol-lyase activities of MC-1061/pSP18 and MC-1061/pSP19 strains were much lower than those of MT-19516 and MT-10519 strains according to the present invention.

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 1368 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
ATGAACTATC CTGCCGAGCC TTTCCGCATT AAAAGTGTTG AAACCGTATC AATGATCTCA      60
CGCGATGAGC GTGTTAAAAA AATGCAAGAA GCGGGCTATA ACACGTTTTT ACTGAATTCA     120
AAGGATATCT ACATCGATCT GCTGACAGAC AGCGGTACAA ATGCCATGAG TGACAAGCAG     180
TGGGCAGGGA TGATGATTGG TGATGAAGCC TACGCAGGCA GTGAAAACTT CTACCATCTC     240
GAAAAAACGG TGAAAGAGTT GTTTGGTTTC AAACACATCG TTCCAACCCA CCAGGGACGC     300
GGGGCGGAAA ACCTGCTCTC GCAGCTGGCC ATTAAGCCCG GTCAATATGT CGCAGGAAAT     360
ATGTACTTTA CAACAACCCG CTTCCATCAG GAAAAAATG GCGCAACCTT TGTGGATATT      420
GTCCGCGATG AAGCACATGA CGCCAGCCTG AATCTCCCCT TTAAAGGTAA TATTGACCTG     480
AATAAATTAG CGACGCTCAT TAAAGAAAAA GGCGCCGAGA ACATCGCCTA TATCTGCCTT     540
GCGGTCACCG TGAATCTGGC GGGTGGGCAG CCTGTTTCAA TGGCGAATAT GCGTGCCGTA     600
CATGAAATGG CCAGCACGTA TGGCATTAAG ATCTATTACG ATGCTACCCG TTGCGTTGAA     660
AATGCCTATT TTATCAAAGA GCAGGAGGCG GGCTACGAGA ACGTCAGTAT CAAAGATATC     720
GTGCATGAAA TGTTCAGCTA TGCCGATGGG TGCACCATGA GCGGTAAAAA AGATTGTCTG     780
GTGAATATCG GCGGCTTCTT GTGTATGAAC GATGAGGAGA TGTTCTCAGC GGCAAAAGAG     840
TTGGTTGTCG TTTATGAAGG TATGCCGTCA TACGGCGGGC TGGCCGGTCG GGATATGGAA     900
GCAATGGCTA TTGGGCTACG TGAAGCCATG CAGTATGAAT ATATTGAACA TCGGGTCAAA     960
CAGGTGCGCT ATCTGGGCGA TAAACTCCGT GAAGCCGGCG TACCCATTGT TGAACCGACG    1020
GGCGGACATG CGGTATTTCT TGATGCTCGT CGTTTCTGTC CACACCTGAC GCAGGATCAG    1080
TTCCCTGCGC AGAGCCTGGC AGCCAGCATC TATATGGAAA CCGGCGTGCG AAGTATGGAA    1140
CGTGGAATTG TTTCCGCCGG TCGTAGCAAG GAAACGGGGG AGAACCATAG CCCCAAACTG    1200
GAGACGGTAC GTCTCACTAT TCCACGCCGT GTTTACACTT ACGCGCACAT GGATGTTATT    1260
GCCGATGGCA TCATTAAACT GTACCAGCAT AAAGAAGATA TTCGTGGTCT GACGTTTGTT    1320
TACGAACCTA AACAACTTCG CTTCTTTACT GCGCGTTTTG ACTTTATT               1368
```

( 2 ) INFORMATION FOR SEQ ID NO:2:

( i ) SEQUENCE CHARACTERISTICS:
        ( A ) LENGTH: 1571 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 176..1543

( x i ) SEQUENCE DESCRIPTION: SEQ ID NO:2:

```
GCGCGCATAG TGACGCGCTA TTTTCACGCA TGATAAATCC CGCATGATGG TGTCGTATTA      60
TTTCCACCTC AATTCTGAGG TTATTGTTAT ATCTTCCTGT GCATTTCATC TATGCACCAG     120
ACTTATTCGA CGCGCATTTT TCTGCGTATG AAAATGGATA ACTGGAGAAA TAAAC ATG     178
```

|     |     |     |     |     |     |     |     |     |     |     |     |     |     |     | Met |     |
|-----|-----|-----|-----|-----|-----|-----|-----|-----|-----|-----|-----|-----|-----|-----|-----|-----|
|     |     |     |     |     |     |     |     |     |     |     |     |     |     |     | 1   |     |
| AAC | TAT | CCT | GCC | GAG | CCT | TTC | CGC | ATT | AAA | AGT | GTT | GAA | ACC | GTA | TCA | 226 |
| Asn | Tyr | Pro | Ala | Glu | Pro | Phe | Arg | Ile | Lys | Ser | Val | Glu | Thr | Val | Ser |     |
|     |     |     | 5   |     |     |     |     | 10  |     |     |     |     | 15  |     |     |     |
| ATG | ATC | TCA | CGC | GAT | GAG | CGT | GTT | AAA | AAA | ATG | CAA | GAA | GCG | GGC | TAT | 274 |
| Met | Ile | Ser | Arg | Asp | Glu | Arg | Val | Lys | Lys | Met | Gln | Glu | Ala | Gly | Tyr |     |
|     |     | 20  |     |     |     |     | 25  |     |     |     |     | 30  |     |     |     |     |
| AAC | ACG | TTT | TTA | CTG | AAT | TCA | AAG | GAT | ATC | TAC | ATC | GAT | CTG | CTG | ACA | 322 |
| Asn | Thr | Phe | Leu | Leu | Asn | Ser | Lys | Asp | Ile | Tyr | Ile | Asp | Leu | Leu | Thr |     |
|     | 35  |     |     |     | 40  |     |     |     |     | 45  |     |     |     |     |     |     |
| GAC | AGC | GGT | ACA | AAT | GCC | ATG | AGT | GAC | AAG | CAG | TGG | GCA | GGG | ATG | ATG | 370 |
| Asp | Ser | Gly | Thr | Asn | Ala | Met | Ser | Asp | Lys | Gln | Trp | Ala | Gly | Met | Met |     |
| 50  |     |     |     | 55  |     |     |     |     | 60  |     |     |     |     | 65  |     |     |
| ATT | GGT | GAT | GAA | GCC | TAC | GCA | GGC | AGT | GAA | AAC | TTC | TAC | CAT | CTC | GAA | 418 |
| Ile | Gly | Asp | Glu | Ala | Tyr | Ala | Gly | Ser | Glu | Asn | Phe | Tyr | His | Leu | Glu |     |
|     |     |     | 70  |     |     |     |     | 75  |     |     |     |     | 80  |     |     |     |
| AAA | ACG | GTG | AAA | GAG | TTG | TTT | GGT | TTC | AAA | CAC | ATC | GTT | CCA | ACC | CAC | 466 |
| Lys | Thr | Val | Lys | Glu | Leu | Phe | Gly | Phe | Lys | His | Ile | Val | Pro | Thr | His |     |
|     |     |     | 85  |     |     |     |     | 90  |     |     |     |     | 95  |     |     |     |
| CAG | GGA | CGC | GGG | GCG | GAA | AAC | CTG | CTC | TCG | CAG | CTG | GCC | ATT | AAG | CCC | 514 |
| Gln | Gly | Arg | Gly | Ala | Glu | Asn | Leu | Leu | Ser | Gln | Leu | Ala | Ile | Lys | Pro |     |
|     |     | 100 |     |     |     |     | 105 |     |     |     |     | 110 |     |     |     |     |
| GGT | CAA | TAT | GTC | GCA | GGA | AAT | ATG | TAC | TTT | ACA | ACA | ACC | CGC | TTC | CAT | 562 |
| Gly | Gln | Tyr | Val | Ala | Gly | Asn | Met | Tyr | Phe | Thr | Thr | Thr | Arg | Phe | His |     |
|     | 115 |     |     |     |     | 120 |     |     |     |     | 125 |     |     |     |     |     |
| CAG | GAA | AAA | AAT | GGC | GCA | ACC | TTT | GTG | GAT | ATT | GTC | CGC | GAT | GAA | GCA | 610 |
| Gln | Glu | Lys | Asn | Gly | Ala | Thr | Phe | Val | Asp | Ile | Val | Arg | Asp | Glu | Ala |     |
| 130 |     |     |     |     | 135 |     |     |     |     | 140 |     |     |     |     | 145 |     |
| CAT | GAC | GCC | AGC | CTG | AAT | CTC | CCC | TTT | AAA | GGT | AAT | ATT | GAC | CTG | AAT | 658 |
| His | Asp | Ala | Ser | Leu | Asn | Leu | Pro | Phe | Lys | Gly | Asn | Ile | Asp | Leu | Asn |     |
|     |     |     |     | 150 |     |     |     |     | 155 |     |     |     |     | 160 |     |     |
| AAA | TTA | GCG | ACG | CTC | ATT | AAA | GAA | AAA | GGC | GCC | GAG | AAC | ATC | GCC | TAT | 706 |
| Lys | Leu | Ala | Thr | Leu | Ile | Lys | Glu | Lys | Gly | Ala | Glu | Asn | Ile | Ala | Tyr |     |
|     |     |     | 165 |     |     |     | 170 |     |     |     |     | 175 |     |     |     |     |
| ATC | TGC | CTT | GCG | GTC | ACC | GTG | AAT | CTG | GCG | GGT | GGG | CAG | CCT | GTT | TCA | 754 |
| Ile | Cys | Leu | Ala | Val | Thr | Val | Asn | Leu | Ala | Gly | Gly | Gln | Pro | Val | Ser |     |
|     |     | 180 |     |     |     |     | 185 |     |     |     |     | 190 |     |     |     |     |
| ATG | GCG | AAT | ATG | CGT | GCC | GTA | CAT | GAA | ATG | GCC | AGC | ACG | TAT | GGC | ATT | 802 |
| Met | Ala | Asn | Met | Arg | Ala | Val | His | Glu | Met | Ala | Ser | Thr | Tyr | Gly | Ile |     |
|     | 195 |     |     |     |     | 200 |     |     |     |     | 205 |     |     |     |     |     |
| AAG | ATC | TAT | TAC | GAT | GCT | ACC | CGT | TGC | GTT | GAA | AAT | GCC | TAT | TTT | ATC | 850 |
| Lys | Ile | Tyr | Tyr | Asp | Ala | Thr | Arg | Cys | Val | Glu | Asn | Ala | Tyr | Phe | Ile |     |
| 210 |     |     |     |     | 215 |     |     |     |     | 220 |     |     |     |     | 225 |     |
| AAA | GAG | CAG | GAG | GCG | GGC | TAC | GAG | AAC | GTC | AGT | ATC | AAA | GAT | ATC | GTG | 898 |
| Lys | Glu | Gln | Glu | Ala | Gly | Tyr | Glu | Asn | Val | Ser | Ile | Lys | Asp | Ile | Val |     |
|     |     |     |     | 230 |     |     |     |     | 235 |     |     |     |     | 240 |     |     |
| CAT | GAA | ATG | TTC | AGC | TAT | GCC | GAT | GGG | TGC | ACC | ATG | AGC | GGT | AAA | AAA | 946 |
| His | Glu | Met | Phe | Ser | Tyr | Ala | Asp | Gly | Cys | Thr | Met | Ser | Gly | Lys | Lys |     |
|     |     |     | 245 |     |     |     |     | 250 |     |     |     |     | 255 |     |     |     |
| GAT | TGT | CTG | GTG | AAT | ATC | GGC | GGC | TTC | TTG | TGT | ATG | AAC | GAT | GAG | GAG | 994 |
| Asp | Cys | Leu | Val | Asn | Ile | Gly | Gly | Phe | Leu | Cys | Met | Asn | Asp | Glu | Glu |     |
|     |     | 260 |     |     |     |     | 265 |     |     |     |     | 270 |     |     |     |     |
| ATG | TTC | TCA | GCG | GCA | AAA | GAG | TTG | GTT | GTC | GTT | TAT | GAA | GGT | ATG | CCG | 1042 |
| Met | Phe | Ser | Ala | Ala | Lys | Glu | Leu | Val | Val | Val | Tyr | Glu | Gly | Met | Pro |     |
|     | 275 |     |     |     |     | 280 |     |     |     |     | 285 |     |     |     |     |     |
| TCA | TAC | GGC | GGG | CTG | GCC | GGT | CGG | GAT | ATG | GAA | GCA | ATG | GCT | ATT | GGG | 1090 |
| Ser | Tyr | Gly | Gly | Leu | Ala | Gly | Arg | Asp | Met | Glu | Ala | Met | Ala | Ile | Gly |     |
| 290 |     |     |     |     | 295 |     |     |     |     | 300 |     |     |     |     | 305 |     |
| CTA | CGT | GAA | GCC | ATG | CAG | TAT | GAA | TAT | ATT | GAA | CAT | CGG | GTC | AAA | CAG | 1138 |

| | | | | | | | | | | | | | | | | |
|---|---|---|---|---|---|---|---|---|---|---|---|---|---|---|---|---|
|Leu|Arg|Glu|Ala|Met|Gln|Tyr|Glu|Tyr|Ile|Glu|His|Arg|Val|Lys|Gln| |
| | | | |310| | | |315| | | | |320| | | |

| | | | | | | | | | | | | | | | | |
|---|---|---|---|---|---|---|---|---|---|---|---|---|---|---|---|---|
|GTG|CGC|TAT|CTG|GGC|GAT|AAA|CTC|CGT|GAA|GCC|GGC|GTA|CCC|ATT|GTT|1186|
|Val|Arg|Tyr|Leu|Gly|Asp|Lys|Leu|Arg|Glu|Ala|Gly|Val|Pro|Ile|Val| |
| | |325| | | |330| | | |335| | | | | | |

| | | | | | | | | | | | | | | | | |
|---|---|---|---|---|---|---|---|---|---|---|---|---|---|---|---|---|
|GAA|CCG|ACG|GGC|GGA|CAT|GCG|GTA|TTT|CTT|GAT|GCT|CGT|CGT|TTC|TGT|1234|
|Glu|Pro|Thr|Gly|Gly|His|Ala|Val|Phe|Leu|Asp|Ala|Arg|Arg|Phe|Cys| |
| | |340| | | |345| | | |350| | | | | | |

| | | | | | | | | | | | | | | | | |
|---|---|---|---|---|---|---|---|---|---|---|---|---|---|---|---|---|
|CCA|CAC|CTG|ACG|CAG|GAT|CAG|TTC|CCT|GCG|CAG|AGC|CTG|GCA|GCC|AGC|1282|
|Pro|His|Leu|Thr|Gln|Asp|Gln|Phe|Pro|Ala|Gln|Ser|Leu|Ala|Ala|Ser| |
| |355| | | | |360| | | |365| | | | | | |

| | | | | | | | | | | | | | | | | |
|---|---|---|---|---|---|---|---|---|---|---|---|---|---|---|---|---|
|ATC|TAT|ATG|GAA|ACC|GGC|GTG|CGA|AGT|ATG|GAA|CGT|GGA|ATT|GTT|TCC|1330|
|Ile|Tyr|Met|Glu|Thr|Gly|Val|Arg|Ser|Met|Glu|Arg|Gly|Ile|Val|Ser| |
|370| | | |375| | | | |380| | | | | |385| |

| | | | | | | | | | | | | | | | | |
|---|---|---|---|---|---|---|---|---|---|---|---|---|---|---|---|---|
|GCC|GGT|CGT|AGC|AAG|GAA|ACG|GGG|GAG|AAC|CAT|AGC|CCC|AAA|CTG|GAG|1378|
|Ala|Gly|Arg|Ser|Lys|Glu|Thr|Gly|Glu|Asn|His|Ser|Pro|Lys|Leu|Glu| |
| | | | |390| | | |395| | | | |400| | | |

| | | | | | | | | | | | | | | | | |
|---|---|---|---|---|---|---|---|---|---|---|---|---|---|---|---|---|
|ACG|GTA|CGT|CTC|ACT|ATT|CCA|CGC|CGT|GTT|TAC|ACT|TAC|GCG|CAC|ATG|1426|
|Thr|Val|Arg|Leu|Thr|Ile|Pro|Arg|Arg|Val|Tyr|Thr|Tyr|Ala|His|Met| |
| | | |405| | | |410| | | | |415| | | | |

| | | | | | | | | | | | | | | | | |
|---|---|---|---|---|---|---|---|---|---|---|---|---|---|---|---|---|
|GAT|GTT|ATT|GCC|GAT|GGC|ATC|ATT|AAA|CTG|TAC|CAG|CAT|AAA|GAA|GAT|1474|
|Asp|Val|Ile|Ala|Asp|Gly|Ile|Ile|Lys|Leu|Tyr|Gln|His|Lys|Glu|Asp| |
| | |420| | | |425| | | |430| | | | | | |

| | | | | | | | | | | | | | | | | |
|---|---|---|---|---|---|---|---|---|---|---|---|---|---|---|---|---|
|ATT|CGT|GGT|CTG|ACG|TTT|GTT|TAC|GAA|CCT|AAA|CAA|CTT|CGC|TTC|TTT|1522|
|Ile|Arg|Gly|Leu|Thr|Phe|Val|Tyr|Glu|Pro|Lys|Gln|Leu|Arg|Phe|Phe| |
|435| | | | | |440| | | | |445| | | | | |

| | | | | | | | |
|---|---|---|---|---|---|---|---|
|ACT|GCG|CGT|TTT|GAC|TTT|ATT|TAATACAACC CTGGCCCCGC AGGGGGCC|1571|
|Thr|Ala|Arg|Phe|Asp|Phe|Ile| | |
|450| | | | |455| | | |

(2) INFORMATION FOR SEQ ID NO:3:

(i) SEQUENCE CHARACTERISTICS:
        (A) LENGTH: 456 amino acids
        (B) TYPE: amino acid
        (D) TOPOLOGY: linear (ii) MOLECULE TYPE: protein (xi) SEQUENCE DESCRIPTION: SEQ ID NO:3:

| | | | | | | | | | | | | | | |
|---|---|---|---|---|---|---|---|---|---|---|---|---|---|---|
|Met|Asn|Tyr|Pro|Ala|Glu|Pro|Phe|Arg|Ile|Lys|Ser|Val|Glu|Thr|Val|
|1| | | |5| | | | |10| | | | |15|

| | | | | | | | | | | | | | | |
|---|---|---|---|---|---|---|---|---|---|---|---|---|---|---|
|Ser|Met|Ile|Ser|Arg|Asp|Glu|Arg|Val|Lys|Lys|Met|Gln|Glu|Ala|Gly|
| | | |20| | | | |25| | | | |30| |

| | | | | | | | | | | | | | | |
|---|---|---|---|---|---|---|---|---|---|---|---|---|---|---|
|Tyr|Asn|Thr|Phe|Leu|Leu|Asn|Ser|Lys|Asp|Ile|Tyr|Ile|Asp|Leu|Leu|
| | |35| | | | |40| | | | |45| | |

| | | | | | | | | | | | | | | |
|---|---|---|---|---|---|---|---|---|---|---|---|---|---|---|
|Thr|Asp|Ser|Gly|Thr|Asn|Ala|Met|Ser|Asp|Lys|Gln|Trp|Ala|Gly|Met|
| |50| | | | |55| | | | |60| | | |

| | | | | | | | | | | | | | | |
|---|---|---|---|---|---|---|---|---|---|---|---|---|---|---|
|Met|Ile|Gly|Asp|Glu|Ala|Tyr|Ala|Gly|Ser|Glu|Asn|Phe|Tyr|His|Leu|
|65| | | | |70| | | | |75| | | | |80|

| | | | | | | | | | | | | | | |
|---|---|---|---|---|---|---|---|---|---|---|---|---|---|---|
|Glu|Lys|Thr|Val|Lys|Glu|Leu|Phe|Gly|Phe|Lys|His|Ile|Val|Pro|Thr|
| | | | |85| | | | |90| | | | |95|

| | | | | | | | | | | | | | | |
|---|---|---|---|---|---|---|---|---|---|---|---|---|---|---|
|His|Gln|Gly|Arg|Gly|Ala|Glu|Asn|Leu|Leu|Ser|Gln|Leu|Ala|Ile|Lys|
| | | |100| | | | |105| | | | |110| |

| | | | | | | | | | | | | | | |
|---|---|---|---|---|---|---|---|---|---|---|---|---|---|---|
|Pro|Gly|Gln|Tyr|Val|Ala|Gly|Asn|Met|Tyr|Phe|Thr|Thr|Thr|Arg|Phe|
| | |115| | | | |120| | | | |125| | |

| | | | | | | | | | | | | | | |
|---|---|---|---|---|---|---|---|---|---|---|---|---|---|---|
|His|Gln|Glu|Lys|Asn|Gly|Ala|Thr|Phe|Val|Asp|Ile|Val|Arg|Asp|Glu|
| |130| | | | |135| | | | |140| | | |

| | | | | | | | | | | | | | | |
|---|---|---|---|---|---|---|---|---|---|---|---|---|---|---|
|Ala|His|Asp|Ala|Ser|Leu|Asn|Leu|Pro|Phe|Lys|Gly|Asn|Ile|Asp|Leu|
|145| | | | |150| | | | |155| | | | |160|

| | | | | | | | | | | | | | | |
|---|---|---|---|---|---|---|---|---|---|---|---|---|---|---|
|Asn|Lys|Leu|Ala|Thr|Leu|Ile|Lys|Glu|Lys|Gly|Ala|Glu|Asn|Ile|Ala|

|       |     |     |     |     |     |     | 165 |     |     |     |     |     | 170 |     |     |     |     |     | 175 |     |
|-------|-----|-----|-----|-----|-----|-----|-----|-----|-----|-----|-----|-----|-----|-----|-----|-----|-----|-----|-----|-----|

Tyr Ile Cys Leu Ala Val Thr Val Asn Leu Ala Gly Gly Gln Pro Val
            180                     185                 190

Ser Met Ala Asn Met Arg Ala Val His Glu Met Ala Ser Thr Tyr Gly
        195                 200                 205

Ile Lys Ile Tyr Tyr Asp Ala Thr Arg Cys Val Glu Asn Ala Tyr Phe
210                     215                 220

Ile Lys Glu Gln Glu Ala Gly Tyr Glu Asn Val Ser Ile Lys Asp Ile
225                 230                 235                 240

Val His Glu Met Phe Ser Tyr Ala Asp Gly Cys Thr Met Ser Gly Lys
                245                 250                 255

Lys Asp Cys Leu Val Asn Ile Gly Gly Phe Leu Cys Met Asn Asp Glu
            260                 265                 270

Glu Met Phe Ser Ala Ala Lys Glu Leu Val Val Val Tyr Glu Gly Met
        275                 280                 285

Pro Ser Tyr Gly Gly Leu Ala Gly Arg Asp Met Glu Ala Met Ala Ile
290                     295                 300

Gly Leu Arg Glu Ala Met Gln Tyr Glu Tyr Ile Glu His Arg Val Lys
305                 310                 315                 320

Gln Val Arg Tyr Leu Gly Asp Lys Leu Arg Glu Ala Gly Val Pro Ile
                325                 330                 335

Val Glu Pro Thr Gly Gly His Ala Val Phe Leu Asp Ala Arg Arg Phe
            340                 345                 350

Cys Pro His Leu Thr Gln Asp Gln Phe Pro Ala Gln Ser Leu Ala Ala
        355                 360                 365

Ser Ile Tyr Met Glu Thr Gly Val Arg Ser Met Glu Arg Gly Ile Val
        370                 375                 380

Ser Ala Gly Arg Ser Lys Glu Thr Gly Glu Asn His Ser Pro Lys Leu
385                 390                 395                 400

Glu Thr Val Arg Leu Thr Ile Pro Arg Arg Val Tyr Thr Tyr Ala His
                405                 410                 415

Met Asp Val Ile Ala Asp Gly Ile Ile Lys Leu Tyr Gln His Lys Glu
            420                 425                 430

Asp Ile Arg Gly Leu Thr Phe Val Tyr Glu Pro Lys Gln Leu Arg Phe
        435                 440                 445

Phe Thr Ala Arg Phe Asp Phe Ile
450                 455

(2) INFORMATION FOR SEQ ID NO:4:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

CCCGGGTATC AACACTGTTA CTGGAGAAAC A        31

(2) INFORMATION FOR SEQ ID NO:5:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(x i) SEQUENCE DESCRIPTION: SEQ ID NO:5:

TATGTTTCTC CAGTAACAGT GTTGATACCC GGGGTAC                37

(2) INFORMATION FOR SEQ ID NO:6:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:6:

GGATAGTTCA TATGTATTTC TCCAG                25

We claim:

1. A cloned tyrosine phenol-lyase gene consisting essentially of a region encoding an amino acid sequence represented by the following formula [I] [SEQ ID NO: 3] which can be expressed in the absence of tyrosine in a culture medium:

Met Asn Tyr Pro Ala Glu Pro Phe Arg Ile Lys Ser Val Glu  [I]

Thr Val Ser Met Ile Ser Arg Asp Glu Arg Val Lys Lys Met

Gln Glu Ala Gly Tyr Asn Thr Phe Leu Leu Asn Ser Lys Asp

Ile Tyr Ile Asp Leu Leu Thr Asp Ser Gly Thr Asn Ala Met

Ser Asp Lys Gln Trp Ala Gly Met Met Ile Gly Asp Glu Ala

Tyr Ala Gly Ser Glu Asn Phe Tyr His Leu Glu Lys Thr Val

Lys Glu Leu Phe Gly Phe Lys His Ile Val Pro Thr His Gln

Gly Arg Gly Ala Glu Asn Leu Leu Ser Gln Leu Ala Ile Lys

Pro Gly Gln Tyr Val Ala Gly Asn Met Tyr Phe Thr Thr Thr

Arg Phe His Gln Glu Lys Asn Gly Ala Thr Phe Val Asp Ile

Val Arg Asp Glu Ala His Asp Ala Ser Leu Asn Leu Pro Phe

Lys Gly Asn Ile Asp Leu Asn Lys Leu Ala Thr Leu Ile Lys

Glu Lys Gly Ala Glu Asn Ile Ala Tyr Ile Cys Leu Ala Val

Thr Val Asn Leu Ala Gly Gly Gln Pro Val Ser Met Ala Asn

Met Arg Ala Val His Glu Met Ala Ser Thr Tyr Gly Ile Lys

Ile Tyr Tyr Asp Ala Thr Arg Cys Val Glu Asn Ala Tyr Phe

Ile Lys Glu Gln Glu Ala Gly Tyr Glu Asn Val Ser Ile Lys

-continued

Asp Ile Val His Glu Met Phe Ser Tyr Ala Asp Gly Cys Thr

Met Ser Gly Lys Lys Asp Cys Leu Val Asn Ile Gly Gly Phe

Leu Cys Met Asn Asp Glu Glu Met Phe Ser Ala Ala Lys Glu

Leu Val Val Val Tyr Glu Gly Met Pro Ser Tyr Gly Gly Leu

Ala Gly Arg Asp Met Glu Ala Met Ala Ile Gly Leu Arg Glu

Ala Met Gln Tyr Glu Tyr Ile Glu His Arg Val Lys Gln Val

Arg Tyr Leu Gly Asp Lys Leu Arg Glu Ala Gly Val Pro Ile

Val Glu Pro Thr Gly Gly His Ala Val Phe Leu Asp Ala Arg

Arg Phe Cys Pro His Leu Thr Gln Asp Gln Phe Pro Ala Gln

Ser Leu Ala Ala Ser Ile Tyr Met Glu Thr Gly Val Arg Ser

Met Glu Arg Gly Ile Val Ser Ala Gly Arg Ser Lys Glu Thr

Gly Glu Asn His Ser Pro Lys Leu Glu Thr Val Arg Leu Thr

Ile Pro Arg Arg Val Tyr Thr Tyr Ala His Met Asp Val Ile

Ala Asp Gly Ile Ile Lys Leu Tyr Gln His Lys Glu Asp Ile

Arg Gly Leu Thr Phe Val Tyr Glu Pro Lys Gln Leu Arg Phe

Phe Thr Ala Arg Phe Asp Phe Ile wherein the 5' end of the tyrosine phenol-lyase gene is covalently attached to a linker of the formula:

5' CCCGGGTATCAACACTGTTACTGGAGAAACA 3'
3' CATGGGGCCCATAGTTGTGACAATGACCTCTTTGTAT 5'.

2. The cloned tyrosine phenol-lyase of claim 1, which has a nucleotide sequence represented by the following formula [III] [SEQ ID. NO: 1]:

ATG AAC TAT CCT GCC GAG CCT TTC CGC ATT AAA AGT GTT GAA  [II]

ACC GTA TCA ATG ATC TCA CGC GAT GAG CGT GTT AAA AAA ATG

CAA GAA GCG GGC TAT AAC ACG TTT TTA CTG AAT TCA AAG GAT

ATC TAC ATC GAT CTG CTG ACA GAC AGC GGT ACA AAT GCC ATG

AGT GAC AAG CAG TGG GCA GGG ATG ATG ATT GGT GAT GAA GCC

TAC GCA GGC AGT GAA AAC TTC TAC CAT CTC GAA AAA ACG GTG

AAA GAG TTG TTT GGT TTC AAA CAC ATC GTT CCA ACC CAC CAG

GGA CGC GGG GCG GAA AAC CTG CTC TCG CAG CTG GCC ATT AAG

-continued

```
CCC GGT CAA TAT GTC GCA GGA AAT ATG TAC TTT ACA ACA ACC
CGC TTC CAT CAG GAA AAA AAT GGC GCA ACC TTT GTG GAT ATT
GTC CGC GAT GAA GCA CAT GAC GCC AGC CTG AAT CTC CCC TTT
AAA GGT AAT ATT GAC CTG AAT AAA TTA GCG ACG CTC ATT AAA
GAA AAA GGC GCC GAG AAC ATC GCC TAT ATC TGC CTT GCG GTC
ACC GTG AAT CTG GCG GGT GGG CAG CCT GTT TCA ATG GCG AAT
ATG CGT GCC GTA CAT GAA ATG GCC AGC ACG TAT GGC ATT AAG
ATC TAT TAC GAT GCT ACC CGT TGC GTT GAA AAT GCC TAT TTT
ATC AAA GAG CAG GAG GCG GGC TAC GAG AAC GTC AGT ATC AAA
GAT ATC GTG CAT GAA ATG TTC AGC TAT GCC GAT GGG TGC ACC
ATG AGC GGT AAA AAA GAT TGT CTG GTG AAT ATC GGC GGC TTC
TTG TGT ATG AAC GAT GAG GAG ATG TTC TCA GCG GCA AAA GAG
TTG GTT GTC GTT TAT GAA GGT ATG CCG TCA TAC GGC GGG CTG
GCC GGT CGG GAT ATG GAA GCA ATG GCT ATT GGG CTA CGT GAA
GCC ATG CAG TAT GAA TAT ATT GAA CAT CGG GTC AAA CAG GTG
CGC TAT CTG GGC GAT AAA CTC CGT GAA GCC GGC GTA CCC ATT
GTT GAA CCG ACG GGC GGA CAT GCG GTA TTT CTT GAT GCT CGT
CGT TTC TGT CCA CAC CTG ACG CAG GAT CAG TTC CCT GCG CAG
AGC CTG GCA GCC AGC ATC TAT ATG GAA ACC GGC GTG CGA AGT
ATG GAA CGT GGA ATT GTT TCC GCC GGT CGT AGC AAG GAA ACG
GGG GAG AAC CAT AGC CCC AAA CTG GAG ACG GTA CGT CTC ACT
ATT CCA CGC CGT GTT TAC ACT TAC GCG CAC ATG GAT GTT ATT
GCC GAT GGC ATC ATT AAA CTG TAC CAG CAT AAA GAA GAT ATT
CGT GGT CTG ACG TTT GTT TAC GAA CCT AAA CAA CTT CGC TTC
TTT ACT GCG CGT TTT GAC TTT ATT
``` wherein the 5' end of the tyrosine phenol-lyase gene is covalently attached to a linker of the formula:

```
5' CCCGGGTATCAACACTGTTACTGGAGAAACA 3'
3' CATGGGGCCCATAGTTGTGACAATGACCTCTTTGTAT 5'.
```

3. A recombinant plasmid comprising the cloned tyrosine phenol lyase gene of claim 1 operatively linked to a promoter, said promoter being selected from the group consisting of trp, lac, tac, and λP$_L$ promoter said recombinant plasmid being capable of producing tyrosine phenol lyase in a host cell in the absence of tyrosine in a culture medium.

4. The recombinant plasmid of claim 3, wherein said promoter is a tac or lac promoter.

5. The recombinant plasmid of claim 3, which is plasmid pCE26.

6. E. coli transformed with the recombinant plasmid of claim 3, which can produce tyrosine phenol-lyase in the absence of tyrosine in a culture medium.

7. The E. coli of claim 6, which is E. coli MT-10519 (FERM BP-3287).

8. A recombinant plasmid comprising the cloned tyrosine phenol lyase gene of claim 1 operatively linked to a promoter, said promoter being selected from the group consisting of trp, lac, tac, and λP$_L$ promoter, said recombinant plasmid being capable of producing tyrosine phenol lyase in a host cell in the absence of tyrosine in a culture medium.

9. A process for producing tyrosine phenol-lyase comprising the steps of culturing said E. coli of claim 6 to accumulate tyrosine phenol-lyase in the culture medium and recovering tyrosine phenol-lyase from the culture medium.

10. The process of claim 9, wherein the E. coli is E. coli MT-10519 (FERM BP-3287).